United States Patent
Bartos

(10) Patent No.: US 9,422,219 B2
(45) Date of Patent: Aug. 23, 2016

(54) PRESSURIZED CRUDE AROMATIC CARBOXYLIC ACID FEED MIXES

(71) Applicant: BP Corporation North America Inc., Naperville, IL (US)

(72) Inventor: Thomas M. Bartos, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/585,579

(22) Filed: Dec. 30, 2014

(65) Prior Publication Data
US 2015/0183709 A1 Jul. 2, 2015

Related U.S. Application Data

(60) Provisional application No. 61/921,706, filed on Dec. 30, 2013.

(51) Int. Cl.
C07C 51/16 (2006.01)
C07C 51/42 (2006.01)
C07C 51/265 (2006.01)
C07C 51/47 (2006.01)
C07C 51/43 (2006.01)

(52) U.S. Cl.
CPC ............... *C07C 51/42* (2013.01); *C07C 51/265* (2013.01); *C07C 51/43* (2013.01); *C07C 51/47* (2013.01)

(58) Field of Classification Search
CPC ...................................... C07C 51/265
USPC ....................................... 562/412
See application file for complete search history.

(56) References Cited

U.S. PATENT DOCUMENTS

| 5,723,656 | A | 3/1998 | Abrams |
| 6,137,001 | A | 10/2000 | Broeker et al. |
| 7,935,844 | B2 | 5/2011 | Bartos |
| 7,935,845 | B2 | 5/2011 | Bartos |
| 8,173,834 | B2 | 5/2012 | Bartos |
| 9,260,370 | B2 | 2/2016 | Bartos |
| 2009/0234156 | A1* | 9/2009 | Bartos ............... B01D 3/009 562/414 |
| 2009/0234256 | A1* | 9/2009 | Helgeson ............ A61H 23/04 601/41 |
| 2015/0183710 | A1 | 7/2015 | Clark et al. |

FOREIGN PATENT DOCUMENTS

| GB | 785045 | 10/1957 | |
| GB | 1047433 | 11/1966 | |
| GB | 2018252 A | * 10/1979 | ........... C07C 51/487 |
| JP | EP 0265137 A2 | * 4/1988 | ........... C07C 51/487 |
| WO | WO-2006/102137 A1 | 9/2006 | |
| WO | WO-2011/041151 A2 | 4/2011 | |
| WO | WO-2011/100682 A2 | 8/2011 | |

* cited by examiner

*Primary Examiner* — Porfirio Nazario Gonzalez
*Assistant Examiner* — Kofi Adzamli
(74) *Attorney, Agent, or Firm* — Robert N. Carpenter

(57) ABSTRACT

Processes for manufacturing a purified aromatic carboxylic acid include heating a purification reaction mixture in a preheating zone, the purification reaction mixture comprising a crude aromatic carboxylic acid and a solvent, and purifying the crude aromatic carboxylic acid in the purification reaction mixture to form a purified aromatic carboxylic acid product. One or more operations are maintained at a pressure above ambient in order to achieve energy savings.

18 Claims, 1 Drawing Sheet

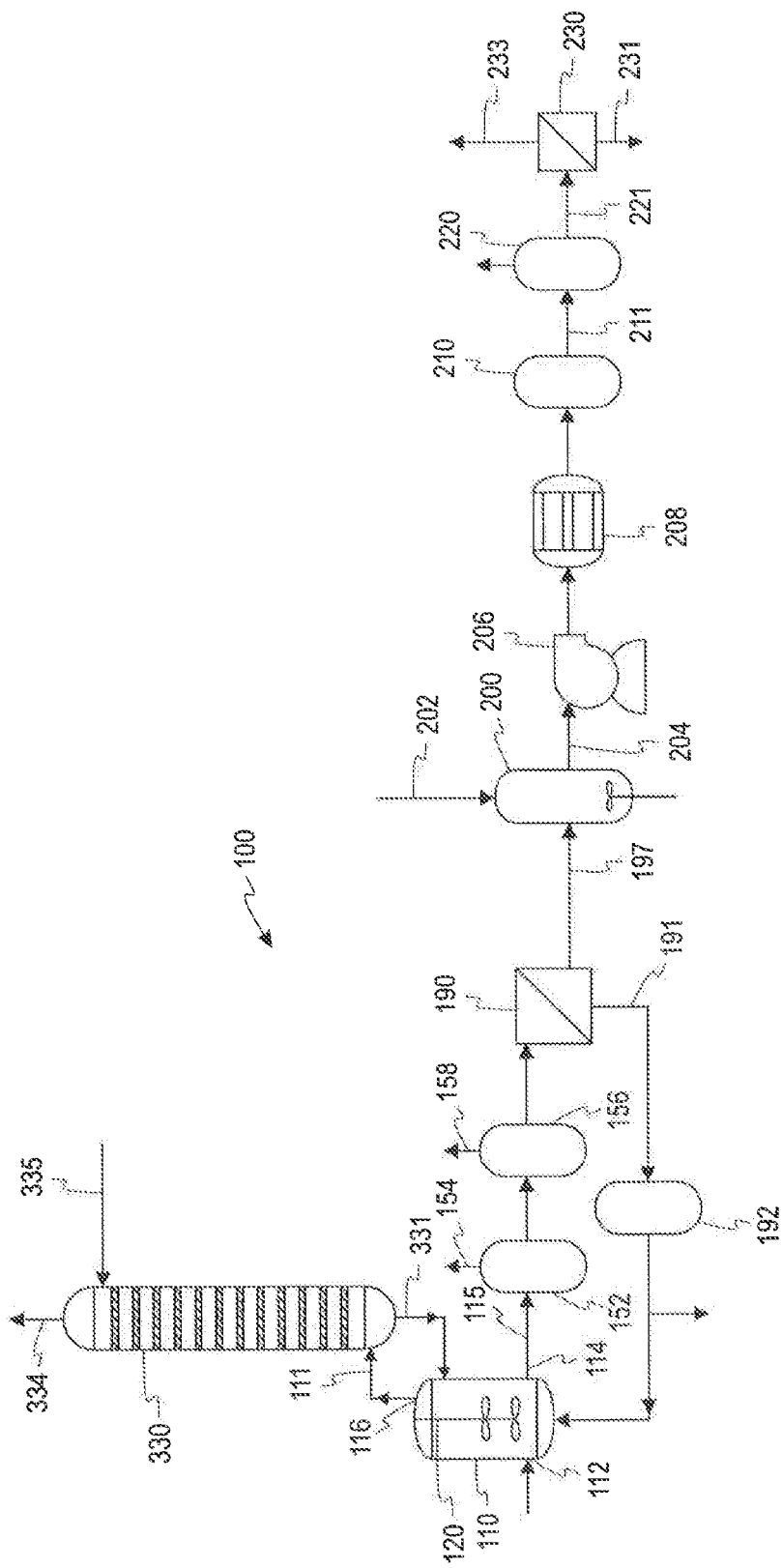

PRESSURIZED CRUDE AROMATIC CARBOXYLIC ACID FEED MIXES

CROSS-REFERENCE TO RELATED APPLICATIONS

This application claims the benefit of priority from U.S. Provisional Application No. 61/921,706, filed Dec. 30, 2013.

TECHNICAL FIELD

The present teachings relate generally to processes for manufacturing aromatic carboxylic acids, and in particular, to processes for preparing crude aromatic carboxylic acids for purification.

BACKGROUND

Terephthalic acid (TA) and other aromatic carboxylic acids may be used in the manufacture of polyesters (e.g., via their reaction with ethylene glycol and/or higher alkylene glycols). Polyesters in turn may be used to make fibers, films, containers, bottles, other packaging materials, molded articles, and the like.

In commercial practice, aromatic carboxylic acids have been made by liquid phase oxidation of methyl-substituted benzene and naphthalene feedstocks in an aqueous acetic acid solvent. The positions of the methyl substituents correspond to the positions of carboxyl groups in the aromatic carboxylic acid product. Air or other sources of oxygen (e.g., typically in a gaseous state) have been used as oxidants in the presence, for example, of a bromine-promoted catalyst that contains cobalt and manganese. The oxidation is exothermic and yields aromatic carboxylic acid together with by-products, including partial or intermediate oxidation products of the aromatic feedstock, and acetic acid reaction products (e.g., methanol, methyl acetate, and methyl bromide). Water is also generated as a by-product.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids having reduced levels of impurities may be made by further oxidizing crude products from liquid phase oxidation as described above at one or more progressively lower temperatures and oxygen levels. In addition, partial oxidation products may be recovered during crystallization and converted into the desired acid product.

Pure forms of terephthalic acid and other aromatic carboxylic acids having reduced amounts of impurities—for example, purified terephthalic acid (PTA)—have been made by catalytically hydrogenating less pure forms of the acids or so-called medium purity products in solution at elevated temperature and pressure using a noble metal catalyst. In commercial practice, liquid phase oxidation of alkyl aromatic feed materials to crude aromatic carboxylic acid, and purification of the crude product, are oftentimes conducted in continuous integrated processes in which crude product from the liquid phase oxidation is used as a starting material for the purification.

In conventional purification units, crude aromatic carboxylic acid is typically mixed with water to form a purification reaction mixture prior to its introduction to the purification reactor. The mixing occurs in a feed mix vessel that is maintained at ambient pressure in order to allow rerun aromatic carboxylic from the vessel and to enable use of a screw conveyor feed of crude aromatic carboxylic from an intermediate silo to the feed mix vessel, which requires the feed mix vessel to be pressure-equilibrated with the silo which operates at ambient pressure. When the feed mix vessel is at ambient pressure, the highest possible temperature of the water in the vessel is about 100° C., the boiling point of water at ambient pressure. The purification reaction mixture must be pre-heated prior to its introduction into the purification reactor, which typically runs at 250° C. to 300° C. This heating required to raise the temperature of the purification reaction mixture from 100° C. or less to at least 250° C. adds to the variable cost of the integrated process for manufacturing purified aromatic carboxylic acids.

There continues to be a need to reduce the overall costs of manufacturing aromatic carboxylic acids.

SUMMARY

The scope of the present invention is defined solely by the appended claims, and is not affected to any degree by the statements within this summary.

According to one aspect of the invention, a process for manufacturing a purified aromatic carboxylic acid is provided. A purification reaction mixture comprising a crude aromatic carboxylic acid and water is pre-heated in a pre-heating zone. The purification reaction mixture enters the pre-heating zone at a pressure above ambient. The crude aromatic carboxylic acid in purification reaction mixture is then purified to form a purified aromatic carboxylic acid product.

According to another aspect of the invention, a process for manufacturing a purified aromatic carboxylic acid is provided. A purification reaction mixture comprising a crude aromatic carboxylic acid and water is pre-heated in a pre-heating zone. The purification reaction mixture enters the pre-heating zone at a temperature above 100° C. The crude aromatic carboxylic acid in purification reaction mixture is then purified to form a purified aromatic carboxylic acid product.

Other aspects of the invention will be apparent to those skilled in the art in view of the description that follows.

BRIEF DESCRIPTION OF THE DRAWINGS

FIG. 1 shows a process flow diagram for manufacturing purified forms of aromatic carboxylic acids in accordance with the present teachings.

DETAILED DESCRIPTION

By way of general introduction, a process for manufacturing a purified aromatic carboxylic acid in accordance with the present invention comprises: heating a purification reaction mixture in a pre-heating zone, the purification reaction mixture comprising a crude aromatic carboxylic acid and water, the purification reaction mixture entering the pre-heating zone at a pressure above ambient; and purifying the crude aromatic carboxylic acid in the purification reaction mixture to form a purified aromatic carboxylic acid product. In some embodiments, the purification reaction mixture also enters the pre-heating zone at temperatures above 100° C., which would not be possible if the purification reaction mixture was maintained at atmospheric pressure prior to being fed into the pre-heating zone. Accordingly, compared with prior processes, less heat is required to raise the temperature in the pre-heating zone to the temperature required by the purification reactor.

In some embodiments, the purification reaction mixture is introduced into pre-heating zone at a pressure that is greater than about 1.0 bar(g), in some embodiments greater than about 2.0 bar(g), in some embodiments greater than about 3.0 bar(g), in some embodiments greater than about 4.0 bar(g), in some embodiments greater than about 5.0 bar(g), and in some embodiments greater than about 6.0 bar(g In some embodiments, the purification reaction mixture is introduced into the pre-heating zone at a temperature that is greater than about 105° C. In some embodiments, the temperature is greater than about 115° C., in some embodiments greater than about 1205° C., in some embodiments greater than about 125° C., in some embodiments greater than about 130° C., in some embodiments greater than about 140° C.

In some embodiments, the process further comprises forming the purification reaction mixture in a mixing by a water containing stream with a slurry comprising crude aromatic carboxylic acid. In some embodiments, the mixing zone is maintained at a at a pressure that is greater than about 1.0 bar(g), in some embodiments greater than about 2.0 bar(g), in some embodiments greater than about 3.0 bar(g), in some embodiments greater than about 4.0 bar(g), in some embodiments greater than about 5.0 bar(g), and in some embodiments greater than about 6.0 bar(g). In some embodiments, the mixing zone is maintained at a temperature that is greater than about 105° C. In some embodiments, the temperature is greater than about 115° C., in some embodiments greater than about 120° C., in some embodiments greater than about 125° C., in some embodiments greater than about 130° C., in some embodiments greater than about 140° C.

In some embodiments, purifying the purification reaction mixture comprises contacting an aqueous solution that comprises at least a portion of the crude aromatic carboxylic acid with hydrogen in the presence of a catalyst.

In some embodiments, the process further comprises oxidizing a substituted aromatic hydrocarbon with gaseous oxygen in a liquid phase oxidation reaction mixture comprising a monocarboxylic acid solvent, water, and a catalyst composition. In some embodiments, the purifying comprises contacting an aqueous solution that comprises at least a portion of the crude aromatic carboxylic acid with hydrogen in the presence of a catalyst.

In some embodiments, the process comprises: oxidizing para-xylene in a reaction zone to form the crude terephthalic acid, wherein the oxidizing comprises contacting the para-xylene with gaseous oxygen in a liquid phase oxidation reaction mixture that comprises acetic acid, water, and a bromine-promoted catalyst composition; crystallizing the crude terephthalic acid, transferring at least a portion of the crude terephthalic acid to a mixing zone maintained at a pressure above ambient temperature and mixing the crude terephthalic acid with a water containing stream to form a purification reaction mixture, introducing the purification reaction mixture to a pre-heating zone and heating the purification reaction mixture to at least 250° C., and purifying the crude terephthalic acid in a hydrogenation reactor by contacting the purification reaction mixture with hydrogen in the presence of a catalyst.

Additional features of the above-described processes for manufacturing purified forms of aromatic carboxylic acid in accordance with the present teachings will now be described in reference to the drawing figures.

FIG. 1 shows a process flow diagram for manufacturing purified forms of aromatic carboxylic acids in accordance with one embodiment of the present invention. As a brief introduction, the process 100 includes an oxidation reactor 110 configured for liquid phase oxidation of feedstock; a crystallization zone configured for forming crude solid product from the liquid phase oxidation reaction mixture, and comprising crystallization vessels 152 and 156; a solid-liquid separation device 190 configured for separating crude solid product (and oxidation by-products) from liquid, a mixing zone including a purification reaction mixture make up vessel 200 configured for preparing mixtures of crude solid product in purification reaction solvent; a pre-heating zone including a heat exchanger 208 for heating the purification reaction mixture prior to its introduction into a purification zone, a purification zone including a purification reactor 210 configured for purifying the crude aromatic carboxylic acid, a crystallization zone including vessel 220 configured for forming purified solid product from the purification solution; and a solid-liquid separation device 230 configured for separating purified solid product from liquid. The integration of processes in FIG. 1 is meant to be purely representative, and various other integrated, and non-integrated configurations may likewise be used.

Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams or compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

Representative aromatic feedstock materials suitable for use in the oxidation reactor 110 include but are not limited to aromatic compounds (e.g., hydrocarbons) substituted at one or more positions with at least one group that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as a hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene; methylacetophenone; 1,2,4-trimethylbenzene; 1-formyl-2,4-dimethyl-benzene; 1,2,4,5-tetramethyl-benzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present teachings are not restricted and include but are not limited to mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) aromatic rings that, in some embodiments, are fused (e.g., naphthalene, anthracene, etc.) and, in other embodiments, are not. In some embodiments, the aromatic carboxylic acid comprises only one carboxylic acid (e.g., —$CO_2H$) moiety or a salt thereof (e.g., —$CO_2X$, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be conducted in the oxidation reactor 110 is a liquid phase oxidation that comprises contacting oxygen gas and a feed material comprising an aromatic hydrocarbon having substituents oxidizable to carboxylic acid groups in a liquid phase reaction mixture. In some embodiments, the liquid phase reaction mixture comprises a monocarboxylic acid solvent and water in the presence of a catalyst composition comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in one or more reactors.

In a representative embodiment, such as may be implemented as shown in FIG. 1, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air may be continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reactor 110, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead vapor phase that comprises vaporized acetic acid, water vapor, gaseous by-products from the oxidation reaction, carbon oxides, nitrogen from the air charged to the reaction, unreacted oxygen, and the like, and combinations thereof.

The overhead vapor may be removed from the reactor through vent 116 and sent in a stream 111 to high-pressure distillation column 330. The separation zone is configured to separate water from the solvent monocarboxylic acid and return a solvent-rich liquid phase to the reactor via line 331. A water rich gas phase is removed from the separation zone via line 334 and for further processed, for example, by recovering energy through an expander, by condensing water from the gas stream for use in the purification zone or other parts of the process, and by treatment of waste gases. Reflux is returned to the column 330 via line 335. The reflux fluid may include condensed portions of the water rich gas stream 334 or may include fluid from other sources. Examples of further processing of the overhead gas stream and sources of reflux fluids are more fully described in U.S. Pat. Nos. 5,723,656, 6,137,001, 7,935,844, 7,935,845, and 8,173,834.

In some embodiments, liquid effluent comprising solid oxidation products slurried in the liquid phase reaction mixture is removed from reaction vessel 110 through slurry outlet 114 and directed in stream 115 to crystallization vessel 152, and in turn crystallization vessel 156, for recovery of a solid product.

In some embodiments, solid crude product may be recovered from the liquid by crystallization in one or more stages, such as in a single crystallization vessel or, as shown in FIG. 1, in a series of multiple stirred crystallization vessels. In some embodiments, the crystallization process comprises sequential reductions in temperature and pressure from earlier to later stages to increase product recovery. By way of example, as shown in FIG. 1, crystallization vessels 152 and 156 may be provided in series and in fluid communication, such that product slurry from vessel 152 may be transferred to vessel 156. Cooling in the crystallization vessels may be accomplished by pressure release. One or more of the crystallization vessels may be vented, as at vents 154 and 158, to remove vapor resulting from pressure let down and generation of steam from the flashed vapor to a heat exchange means (not shown).

As shown in FIG. 1, the crystallization vessel 156 is in fluid communication with a solid-liquid separation device 190. The solid-liquid separation device 190 is configured to receive a slurry of solid product from the crystallization vessel 156. In some embodiments, the solid-liquid separation device 190 is further configured to separate a crude solid product and by-products from the liquid. In some embodiments, the separation device 190 is a centrifuge, a rotary vacuum filter, a pressure filter, or the like, or a combination thereof. In some embodiments, the separation device 190 comprises a pressure filter configured for solvent exchange (e.g., by positive displacement under pressure of mother liquor in a filter cake with wash liquid comprising water). The oxidation mother liquor resulting from the separation may exit separation device 190 in stream 191 for transfer to mother liquor drum 192. A portion of the mother liquor and, in some embodiments, a major portion of the mother liquor, may be transferred from drum 192 to oxidation reactor 110. In such a way, monocarboxylic acid solvent, water, catalyst, and/or oxidation reaction by-products dissolved and/or present as fine solid particles in the mother liquor may be returned to the liquid phase oxidation reaction.

As shown in FIG. 1, the stream 197 comprising heated crude solid product may be directed to a mixing zone including a reaction mixture make up vessel 200. The crude solid product in stream 197 may be mixed and slurried in make up vessel 200 in with a make-up solvent entering vessel 200 through line 202 to form a purification reaction mixture. In some embodiments, the purification make-up solvent contains water. In some embodiments, the solvent line 202 connects to a holding vessel (not shown) for containing make-up solvent. In other embodiments, the solvent comprises fresh demineralized water fed from a deaerator. In other embodiments, the solvent is supplied from another part of the integrated process 100. For example, in one embodiment, the solvent comprises the condensate obtained from an off-gas separation in column 330 or from vapors recovered from a crystallization zone Sources of purification make-up solvent are more fully described, for example, in U.S. Pat. Nos. 5,723,656, 6,137,001, 7,935,844, 7,935,845, and 8,173,834.

The mixing zone is configured to operate at a pressure above ambient. This pressure is maintained in vessel 200 by sealing the inlet lines 197 and 202 with pumps, filters, control valves or rotary valves (not shown) and outlet line 204 with pump 206. In one embodiment, the pressure sealing of vessel 200 is accomplished by providing a rotary pressure filter as solid-liquid separation 190. The rotary pressure filter pressurizes the discharged slurry exiting the device 190 and entering line 197. Suitable rotary pressure filters are sold by BHS-Sonthofen and are disclosed for example, in U.S. Pat. Nos. 2,741,369, 7,807,060 and US Pat. App. 20050051473. Purification reaction mixture is prepared in vessel 200 is withdrawn through line 204 and transferred to pump 206, which also acts to maintain the pressure in vessel 200. By maintaining the vessel 200 at a pressure above ambient pressure, the purification make-up solvent 202 can enter the vessel 200 and be maintained in the vessel 200 at a pressure above ambient, and therefore may enter and be maintained at a temperature higher than would be possible than if the vessel were maintained at ambient temperature. For example, water in the purification make-up solvent could only be added to vessel at a maximum of 100° C. if the vessel were maintained at one atmosphere absolute pressure. By allowing purification make-up solvent to have a higher pressure and temperature when entering the vessel 200, the resulting purification reaction mixture formed in the vessel 200 will have a higher temperature than would be possible if the vessel 200 were not maintained at pressure.

Suitable sources of pressurized purification make-up solvent include demineralized water, steam condensate, condensate from distillation in the oxidation section, such as overhead condensed from stream 334, and condensate from purification crystallizers such as 220.

Purification reaction mixture exiting vessel 200 through line 204 enters a pre-heating zone. The purification reaction mixture is introduced into the pre-heating zone at a pressure above ambient, which allows the purification reaction mixture to be introduced at a higher temperature than would have been possible if non-pressurized. The pre-heating zone shown in FIG. 1 includes a pump 206 and a heat exchanger 208. Those skilled in the art will appreciate that although only one heat exchanger is shown in FIG. 1, the pre-heating zone may include additional heat exchangers configured in series or parallel. The heat exchanger 208 raises the temperature of the purification reaction mixture to a temperature required for a purification reaction as described below. In one embodiment, the temperature is raised to at least 250° C. In one embodiment, the temperature is raised to about 290° C. Because the purification reaction mixture enters at a higher temperature than in conventional, non-pressurized systems, the energy required for heating the purification reaction mixture in the pre-heating zone is less than would be required for the conventional, non-pressurized systems.

The heated purification reaction mixture exits the pre-heating zone and enters the purification zone. The purification zone includes a purification reactor 210. In some embodiments, purification in the purification reactor 210 comprises contacting the purification reaction mixture with hydrogen at elevated temperature and pressure in the presence of a hydrogenation catalyst. In some embodiments, the pressure ranges from about 85 to about 95 kg/cm$^2$. In some embodiments, a portion of the purification liquid reaction mixture may be continuously removed from hydrogenation reactor 210 in stream 211 and directed to a crystallization vessel 220 in a downstream crystallization zone. In crystallization vessel 220, terephthalic acid and reduced levels of impurities may be crystallized from the reaction mixture (e.g., by reducing pressure on the liquid). The resulting slurry of purified terephthalic acid and liquid formed in vessel 220 may be directed to solid-liquid separation device 230 in stream 221. Vapors resulting from pressure letdown in the crystallization reactor 220 may be condensed by passage to heat exchangers (not shown) for cooling. The resulting condensate liquid may be redirected to the process, for example as recycle to purification feed makeup tank (not shown), through suitable transfer lines (not shown) and/or be directed to waste water treatment (WWT). Purified terephthalic acid exits solid-liquid separation device 230 in the stream 231. In some embodiments, at least a portion, in some embodiments all or substantially all, of the purification mother liquor may be directed in stream 233 as reflux to high-pressure distillation column 330, as more fully described, for example, in U.S. Pat. Nos. 5,723,656, 6,137,001, 7,935,844, 7,935,845, and 8,173,834. In other embodiments, stream 233 may be directed to a waste water treatment facility. The solid-liquid separation device 230 may be a centrifuge, a rotary vacuum filter, a pressure filter, or the like, or a combination thereof.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for manufacturing a purified aromatic carboxylic acid comprising:
   heating a purification reaction mixture in a pre-heating zone; the purification reaction mixture comprising a crude aromatic carboxylic acid and solvent, the purification reaction mixture entering the pre-heating zone at a pressure above ambient; and
   purifying the crude aromatic carboxylic acid in the purification reaction mixture in a purification zone to form a purified aromatic carboxylic acid product.

2. A process for manufacturing a purified aromatic carboxylic acid comprising:
   heating a purification reaction mixture in a pre-heating zone; the purification reaction mixture comprising a crude aromatic carboxylic acid and solvent, the purification reaction mixture entering the pre-heating zone at a temperature above 100° C.; and
   purifying the crude aromatic carboxylic acid in the purification reaction mixture in a purification zone to form a purified aromatic carboxylic acid product.

3. A process for manufacturing a purified aromatic carboxylic acid comprising:
   mixing crude aromatic carboxylic acid and a solvent in a mixing zone to form purification reaction mixture, the solvent being fed to the mixing zone at a pressure above ambient;
   heating a purification reaction mixture in a pre-heating zone; the purification reaction mixture comprising a crude aromatic carboxylic acid and solvent, the purification reaction mixture entering the pre-heating zone at a temperature above 100° C.; and
   purifying the crude aromatic carboxylic acid in the purification reaction mixture in a purification zone to form a purified aromatic carboxylic acid product.

4. The process of claim 1, further comprising:
   forming the purification reaction mixture in mixing zone by mixing a solvent with a stream comprising crude aromatic carboxylic acid.

5. The process of claim 4, wherein the solvent enters the mixing zone at a pressure above ambient.

6. The process of claim 3 or 5, wherein solvent enters the mixing zone at a pressure of at least 1 bar(g).

7. The process of claim 3 or 5, wherein the solvent containing stream enters the mixing zone at a pressure of at least 2 bar(g).

8. The process of claim 3 or 4, wherein the solvent containing stream enters the mixing zone at temperature above 100° C.

9. The process of claim 3 or 4, wherein the solvent containing stream enters the mixing zone at a temperature of at least 120° C.

10. The process of claim 3 or 4, wherein the mixing zone is maintained at a pressure of at least 2 bar(g).

11. The process of claim 1, 2, or 3, wherein the purification reaction mixture enters the pre-heating zone at a pressure of at least 80 bar(g).

12. The process of claim 1 or 2, wherein the purification reaction mixture enters the pre-heating zone at a temperature above 100° C.

13. The process of claim 1, 2, or 3 wherein the purification reaction mixture enters the pre-heating zone at a temperature of at least 120° C.

14. The process of claim 1, 2, or 3 wherein the aromatic carboxylic acid comprises terephthalic acid.

15. The process of claim 1, 2, or 3 further comprising:
   oxidizing a substituted aromatic compound in a reaction zone to form the crude aromatic carboxylic acid;
   transferring effluent from the reaction zone to a crystallization zone; and
   recovering at least a portion of the crude aromatic carboxylic as a solid from the crystallization zone;
   transferring effluent from the crystallization zone to a solid-liquid separation device, wherein the solid-liquid separation device is configured for operation above ambient pressure.

16. The process of claim 15 wherein the solid-liquid separation device comprises a rotary pressure filter.

17. The process of claim 1, 2, or 3 wherein the purification zone comprises a hydrogenation reactor, and wherein the purifying comprises contacting an aqueous solution that comprises at least a portion of the crude aromatic carboxylic acid with hydrogen in the presence of a catalyst.

18. The process of claim 1, 2, or 3 wherein the solvent comprises water.

* * * * *